United States Patent [19]

Mack

[11] Patent Number: 4,941,827
[45] Date of Patent: Jul. 17, 1990

[54] TOOTH FASTENING PLUG FOR A PATTERN

[76] Inventor: Heinz Mack, Sudl. Auffahrtsallee 64, 8000 Munich 19, Fed. Rep. of Germany

[21] Appl. No.: 329,810

[22] Filed: Mar. 28, 1989

[30] Foreign Application Priority Data

Mar. 29, 1988 [DE] Fed. Rep. of Germany ....... 3810690

[51] Int. Cl.⁵ .................................. A61C 19/00
[52] U.S. Cl. .................................... 433/74
[58] Field of Search .......................... 433/74

[56] References Cited

U.S. PATENT DOCUMENTS 3,153,283 10/1964 Weissman ............................ 433/74
3,470,614 10/1969 Kelly ................................... 433/74
4,060,899 12/1977 Sauter ................................. 433/74
4,363,625 12/1982 Avanessian ........................ 433/74

Primary Examiner—John J. Wilson
Attorney, Agent, or Firm—Larson and Taylor

[57] ABSTRACT

A plug connection for fastening tooth or jaw segments to a pattern base is provided which consists of a pin and a matching sleeve which snugly receives the pin and from which the pin can be separated again by counterpressure. The pin consists of a permanently lockable locking shank and of a detachable plug-in shank. The plug-in shank has two different coupling regions which, on the one hand, warrant precise fit of the plug-in shank in the matching sleeve and which, on the other hand, allow perfect uncoupling.

9 Claims, 1 Drawing Sheet

TOOTH FASTENING PLUG FOR A PATTERN

FIELD OF THE INVENTION

The present invention relates to a plug connection for fastening tooth or jaw segments to a pattern base, said connection consisting of a pin and a matching sleeve in which said pin is firmly seated and wherefrom it can be separated by counterpressure.

BACKGROUND OF THE INVENTION

In known plug connections of this type the portion of the pin inserted into the sleeve, i.e. the plug shank, is either of cylindrical or of conical shape, and the interior of the sleeve into which the pin is inserted is shaped cylindrical or conical to match the shape of the pin shank. The pin can be a single pin or a forked pin.

Conical pins have the disadvantage that the elimination of the locking force between shank and sleeve is effected directly in the beginning of lift-off of the respective tooth or jaw segment, i.e. the frictional engagement is eliminated at the moment when the segment is lifted. Moreover, the conical embodiment, on the one hand, effects harsh friction in the final position and, on the other hand, insufficiently safeguarded retention prior to or during lifting of the tooth or jaw segment.

In contrast thereto, the cylindrical plug shanks—even though there the engagement between plug shank and sleeve also extends along the length of a long shank— show that complete elimination of the locking force between plug shank and sleeve is achieved only when the plug shank is completely withdrawn from the sleeve—i.e. in order to completely overcome the adhesive force between plug shank and sleeve it is necessary to completely lift off the tooth or jaw segment along the full length of the pin shank. Aside from the considerable force required for dislodging the tooth or jaw segments from the pattern-base, segments including a plurality of pins, or composite patterns on tooth stumps, are highly prone to misalignment which may be due to even minor irregularities in the parallel alignment produced in drilling the locking hole or gluing the locking shank in position. This usually occurs in divergent or convergent stump preparations or tooth axis positions.

SUMMARY OF THE INVENTION

Therefore, it is the object of the present invention to provide a plug connection with which, on the one hand, the bond strength between plug-in shank and sleeve is not exerted directly, as with a cone, at the start of lift-off of the tooth or jaw segment and, on the other hand, to avoid the disadvantages encountered when there is friction all over the region of the cylindrical plug-in shank, which is fully eliminated only at the instant the plug-in shank is completely removed from the sleeve.

According to the present invention, this problem is solved in that (a) the detachable plug shank of the pin consists of a coupling region of larger cross section disposed in the vicinity of the locking shank and, adjacent thereto, of a coupling region of a cross section smaller than that of the larger cross section, at least either the larger coupling region or the smaller coupling region being of cylindrical configuration, and (b) the sleeve consists of a larger hollow cylindrical region having an internal diameter matching the diameter of the smaller coupling region.

DETAILED DESCRIPTION OF THE PREFERRED EMBODIMENT

The invention will now be explained with reference to FIGS. 1 and 2 without being restricted thereto, however. The details of the invention discernible from FIGS. 1 and 2 showing a preferred embodiment of the pin 1 and of the sleeve 2 in greatly enlarged scale represent preferred features.

Figure 1:
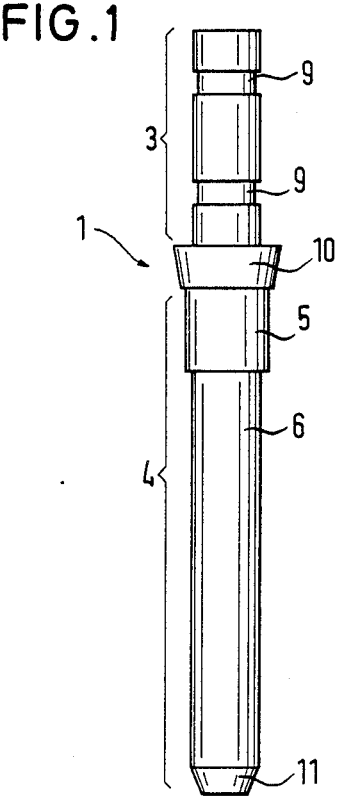
FIG. 1 is a side elevational view of the pin of the present invention.
Figure 2:
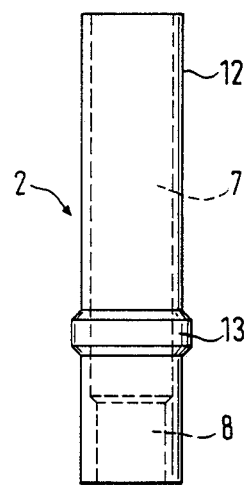
FIG. 2 is a side elevational view of the sleeve of the present invention.

In FIGS. 1 and 2 and in the corresponding parts of the description the numerals referring to the drawings have the following meanings:

1: pin
2: sleeve
3: permanently lockable locking shank
4: detachable plug-in shank
5: larger coupling region
6: smaller coupling region
7: larger hollow cylinder region
8: smaller hollow cylinder region
9: retention depressions
10: conical sleeve
11: land
12: sleeve wall
13: annular bead From FIG. 1 it is apparent that the coupling region 6 of smaller cross section is longer than the larger coupling region 5; however, the "true" coupling region 6 is just as long as the larger coupling region 5. Owing to this construction the smaller coupling region 6 is disengaged to the same extent as the larger coupling region 5 as the plug-in shank 4 is pulled out of the sleeve 2. Preferably both coupling regions 5, 6 are of cylindrical configuration, although it is possible, of course, to make one coupling region cylindrical and the other one conical.

Preferably also the locking shank 3 is of equal or somewhat smaller diameter than the smaller coupling region 6, although it may also be larger. Preferably the locking shank 3 is of equal or somewhat smaller diameter than the smaller coupling region 6, although it may also be larger. Preferably the locking shank 3 is glued into holes previously drilled into the underside of the tooth or jaw pattern. For this purpose the locking shank 3 preferably has one or more retention depressions 9, preferably in the form of annular grooves.

The larger coupling region 5 preferably has a larger diameter than the cylindrical locking shank 3 since the thereby formed step guarantees that the pins always extend with equal length from the bottom of the tooth or jaw pattern and are precisely aligned. Of course, the diameter of the larger coupling regin 5 can also be less than that of the locking shaft 3; however, in that case it is suitable in any event to provide between locking shaft 3 and larger coupling region 5 an annular or conical sleeve 10 of a diameter larger than that of the locking shank 3; also in this way a step is formed which likewise guarantees that the pins extend equally in their axial direction from the tooth or jaw pattern and are precisely aligned.

In order to facilitate the insertion of the plug-in shank 4 into the sleeve 2 one end of the smaller coupling region 6 is preferably provided with a guide land 11. Of course, it is also possible to omit the guide land 11 at the plug-in shank 4. In that case, however, it is advantageous to provide the larger and the smaller hollow cylinder regions 7, 8 with corresponding oppositely shaped guide lands at the locations where the coupling regions 5, 6 first come into contact with the hollow cylinder regions 7, 8.

The sleeve 2 is preferably as long as the entire plug-in shank, 4, less the guide land 11. Furthermore, the wall 12 of the sleeve 2 is provided at least at one point with an annular bead 13 in order to improve retention relative to the material of the pattern base.

The pin 1 preferably consists of metal, especially of brass, while the sleeve 2 preferably is made of synthetic material, although it also may be made of metal (e.g. of brass).

In practice the pin shown in FIG. 1 and constituting a preferred embodiment of the invention has a total length of about 18 mm; the diameter of the locking shank 3 and of the smaller coupling region 6 is about 1.5 to 2 mm. The locking shank has a length of about 5 mm, the annular bead has a length of about 1 mm, the plug-in shank has a length of about 11 mm, and the guide land has a length of about 1 mm. The sleeve 2 has a total length of about 11 mm. The larger coupling region 5 and the smaller hollow cylindrical region 8 each have a length of about 2 mm.

The preferred embodiment of the invention offers the following advantages over the initially described cylindrical and conical pin systems:

(a) The frictional forces are overcome already when the tooth or jaw segment has been lifted about 2 mm, since then both the larger coupling region 5 and the smaller coupling region 6 have been pulled out of the larger hollow cylinder region 7 and the smaller hollow cylinder region 8.

(b) The exact fit is effected by friction both between the larger coupling region 5 and a portion of the interior wall of the larger hollow cylinder region 7, and also between a portion of the smaller coupling region 6 and the interior wall of the smaller hollow cylinder region 8.

(b) The exact fit is effected by friction both between the larger coupling region 5 and a portion of the interior wall of the larger hollow cylinder region 7, and also between a portion of the smaller coupling region 6 and the interior wall of the smaller hollow cylinder region 8.

(c) The guide land 11 serves to center the pin while the plug-in shank 4 is inserted into the sleeve 2 in the pattern base.

(d) The conical sleeve 10 prevents splintering on the surface of the pattern base as the tooth or jaw pattern is lifted off and the plug-in shanks 4 are reinserted into the sleeves 2.

(e) The upper side of the conical sleeve 10 facing the locking shank 3 offers a wide abutment face warranting precise centering as the locking shank 3 is glued into the tooth or jaw model.

(f) The locking shaft 3 displaces the glue as it is inserted into the bore in the tooth or jaw pattern, and the annular retention grooves 9 accommodate the displaced glue thereby providing safe support against vertically acting forces as the jaw or tooth segments are removed and reinserted from and into the pattern base, respectively.

I claim:

1. A plug connection for fastening tooth or jaw segments to a pattern base, said connection comprising a pin and a matching sleeve in which the pin is firmly seated and wherefrom it can be separated again by counter-pressure, said pin comprising a permanently lockable locking shank and a detachable plug-in shank, wherein;
    the detachable plug-in shank of the pin comprises a coupling regin of larger cross-section and an adjacent coupling region of a cross-section smaller than that of the larger cross-section coupling region, and at least either the larger cross-section coupling region or the smaller cross-section coupling region being of cylindrical configuration,
    the sleeve comprising a larger cross-section hollow cylindrical region with an inner diameter corresponding to the cross-section of the larger cross-section coupling region of the pin and a smaller cross-section hollow cylindrical region corresponding to the cross-section of the smaller cross-section coupling region of the pin,
    the axial length of the larger cross-section coupling region of the pin being equal to the length of the smaller cross-section hollow cylindrical region of the sleeve, and
    the smaller cross-section coupling region of the pin being longer than the larger cross-section coupling of the pin and longer than the smaller cross-section hollow cylindrical region of the sleeve.

2. A plug connection according to claim 1, wherein the pin has a total length of about 18 mm; the diameter of the locking shank and of the smaller coupling region of the pin being about 1.5 to 2 mm; the locking shank having a length of about 5 mm, an annular bead on the outside of the sleeve having an axial length of about 1 mm, the plug-in shank having a length of about 11 mm, a guide land on the end of the smaller coupling region of the pin having a length of about 1 mm; the sleeve having a total length of about 11 mm and the larger coupling region of the pin and the smaller hollow cylindrical region of the sleeve each having a length of about 2 mm.

3. A plug connection according to claim 1, wherein both the locking shaft and the larger and smaller coupling regions of the pin are of cylindrical shape.

4. A plug connection according to claim 1, wherein the cylindrical locking shank and the smaller cylindrical coupling region have the same diameters.

5. A plug connection according to claim 1, wherein the locking shank has at least one retention recess.

6. A plug connection according to claim 1, wherein a conical sleeve is provided between the locking shank and the plug-in shank.

7. A plug connection according to claim 1, wherein at least one of the lower ends of the pin or the upper end of the sleeve has a guide land.

8. A plug connection according to claim 1, including an annular bead on the outside of the sleeve.

9. A plug connection according to claim 1, wherein the sleeve length corresponds to the length of the larger end smaller coupling regions of the pin.

* * * * *